US00PP11557P

United States Patent [19]

Jonkers

[11] Patent Number: Plant 11,557

[45] Date of Patent: Oct. 10, 2000

[54] IMPATIENS PLANT NAMED 'FIFY VIOLET'

[75] Inventor: J. B. (Hanneke) Jonkers, Hoorn, Netherlands

[73] Assignee: Goldsmith Plants, Inc., Gilroy, Calif.

[21] Appl. No.: 09/078,656

[22] Filed: May 14, 1998

[51] Int. Cl.[7] ..... A01H 5/00

[52] U.S. Cl. ..... Plt./317

[58] Field of Search ..... Plt./317

*Primary Examiner*—Howard J. Locker
*Assistant Examiner*—Kent L. Bell
*Attorney, Agent, or Firm*—Rothwell, Figg, Ernst & Manbeck

[57] ABSTRACT

A new and distinct cultivar of Impatiens plant, and named 'Fify Violet' is provided. 'Fify Violet' is distinct in its violet flower color, small slightly cup shaped flowers, early flowering and small-leafed basal branching growth habit.

3 Drawing Sheets

BACKGROUND OF THE NEW PLANT

The present invention comprises a new and distinct cultivar of impatiens, botanically known as *Impatiens walleriana*, and herein referred to by the cultivar name 'Fify Violet', and is characterized by the following combinations of repeatedly observed traits:

1. Very free flowering,
2. Small, single, slightly cup shaped flowers,
3. Basal branching with small leaves, and
4. Early flowering.

Asexual reproduction of this cultivar by stem cuttings taken during November, 1996, at Andijk, The Netherlands, has demonstrated that the characteristics of the new cultivar as herein described are firmly fixed and are retained through successive generations of such asexual propagation, such reproduction establishing that the plant does in fact maintain the characteristics described in successive generations. The female parent (i.e., the seed parent) was an *Impatiens walleriana* named IN-1796-3 (unpatented) and the male parent (i.e., pollen parent) was an *Impatiens walleriana* named IN-1444-1 (unpatented). The cross was made in 1995 and the seedling was selected in 1996.

This new cultivar has been identified as Impatiens 'Fify Violet'. The new cultivar is being marketed under the trademark name Firefly Violet.

DESCRIPTION OF THE PHOTOGRAPHS

This new impatiens plant is illustrated by the accompanying photographic drawings in full color, the colors shown being as true as can be reasonably obtained by conventional photographic procedures.

DESCRIPTION OF THE NEW CULTIVAR

Figure 1:
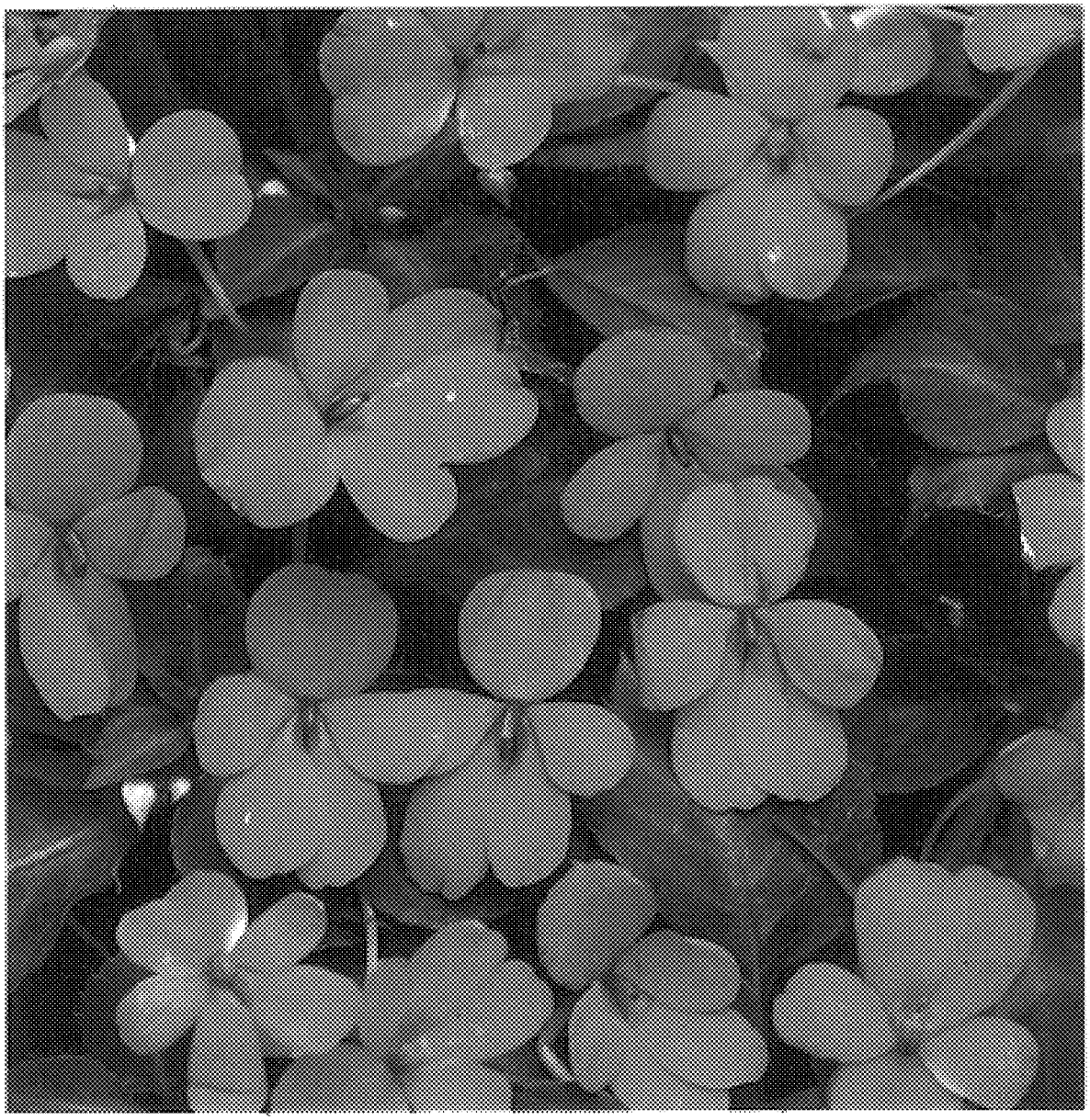
FIG. 1 shows the buds, flowers, and foliage.
Figure 2:
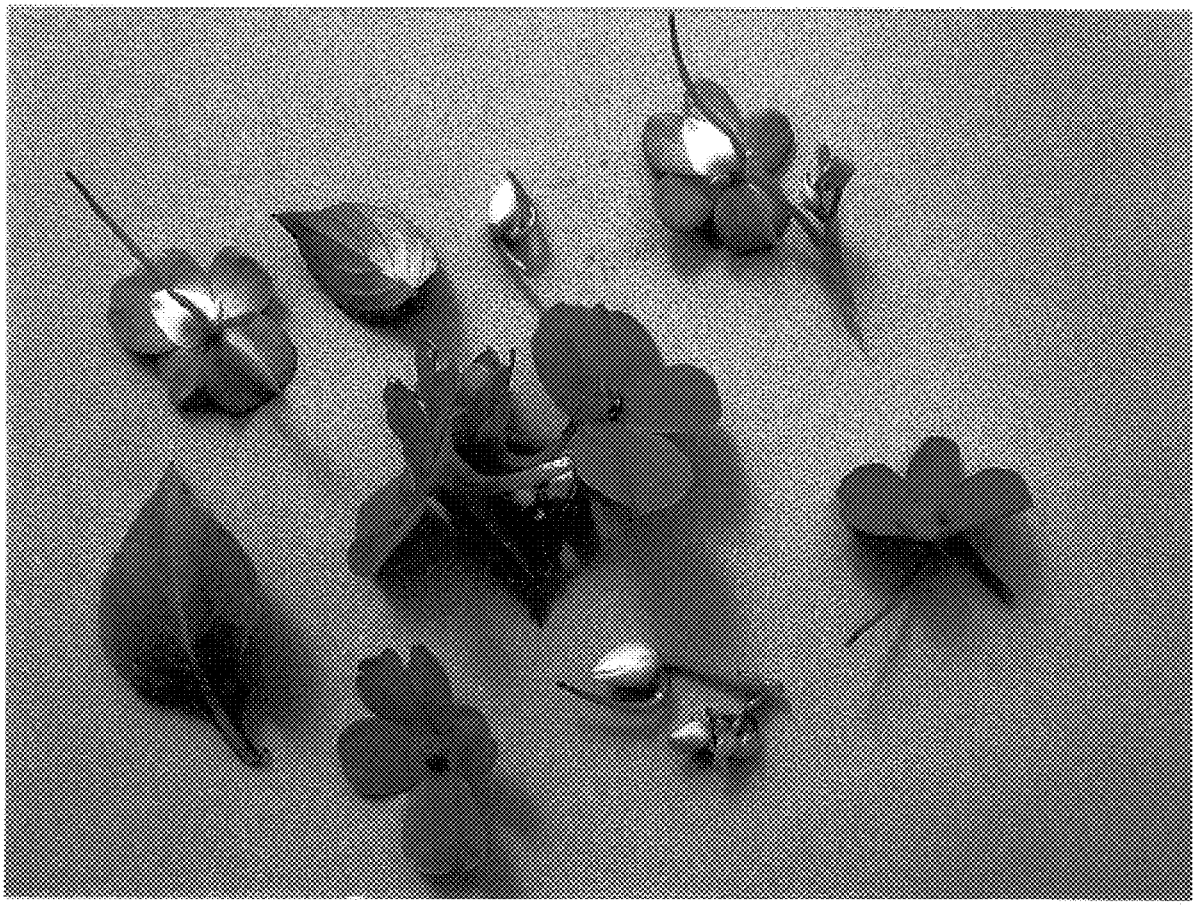
FIG. 2 shows buds and the upper and lower sides of flower and foliage.
Figure 3:
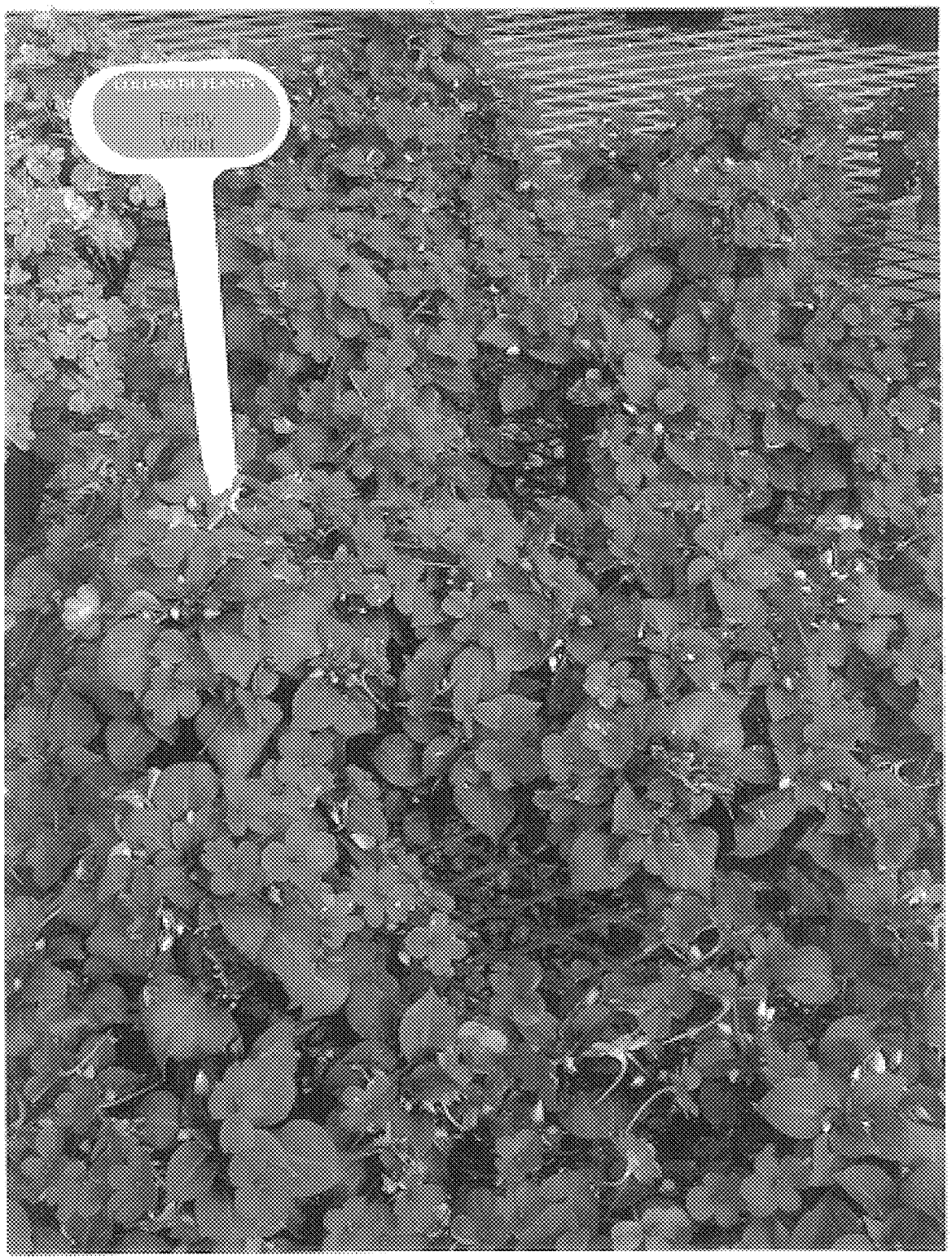
FIG. 3 shows a top perspective view of typical plants of the new cultivar.

The following observations and measurements describe plants grown outside in the field in Andijk, The Netherlands. Measurements were recorded in August, 1997, on plants approximately 14 weeks old. Fully developed organs were used for measurements and color descriptions, unless otherwise indicated. Color references are made to the R.H.S. Colour Chart of The Royal Horticultural Society, London, England, except where general color terms of ordinary significance are used.

'Fify Violet' has not been observed under all possible environmental conditions. The phenotype may vary with variations in environment and horticultural practices, such as temperature, light intensity, day length, fertilization and propagation procedure, without any change in genotype.

Parentage:

*Female parent.*—*Impatiens walleriana* IN-1796-3 (unpatented).

*Male parent.*—*Impatiens walleriana* IN-1444-1 (unpatented).

Propagation:

*Type cutting.*—Stem (internodal) cutting with two nodes and attached leaves.

*Time to initiate roots.*—10–14 days at 70–75 degrees F. with a fully developed root mass at 21 days.

*Rooting habit.*—Fibrous, branching, adventitious root system.

Plant description:

*Form.*—Upright.

*Growth habit.*—Upright branching plant habit with upper leaves and flowers produced in whorls. When grown in a 4 inch pot for 10–12 weeks the height is approximately 3–4 inches and the width is approximately 4 inches.

*Foliage description.*—Leaves are simple. Lower leaf arrangement is alternate with upper leaves arranged in whorls of 5. Leaf shape is lanceolate to elliptic with acute apex and acute base. Leaf size is 3.5 cm×2 cm. Leaf margin is crenate with ciliation. Leaf surface is glabrous. Leaf color is green. The upper surface is yellow-green group 147A. Under surface is yellow-green group 147B. Venation is pinnate 147A for the upper surface and 147B for the lower surface.

*Petiole.*—Petiole length is 2 cm; and diameter is 0.2 cm; Color is yellow-green 147C.

Flower description:

*Flowering habit.*—Rooted cutting to full flowering plant in six weeks. Indeterminate, flowering continuously. Flowers develop in the upper leaf axils.

*Natural flowering season.*—Flowers continuously throughout the year.

*Flowers borne.*—Singly on pedicels which are yellow-green 145A and 1–1.5 cm long in clusters of 2–7 flowers with a peduncle color of yellow-green 145A and length of 1–1.5 cm long.

*Spur*.—Short spurred; length is 3 cm; color is 57C.

*Buds*.—Buds are oval-shaped at first color 74A; size is 0.8 cm×0.5 cm.

*Quantity of flowers*.—Floriferous. Each axillary cluster of 2–7 flowers developing progressively from the leaf whorls so that buds as well as mature flowers are visible at the same time in large numbers.

*Petals*.—Number of petals 5, with all petals overlapping consisting of 1 round petal approximately 1 cm and 4 oval petals approximately 1.5 cm length and 0.8 cm width. Top three petals are slightly cupped.

*Flower color*.—Upper surface: Red-purple group 74A. Lower surface: Red-purple group 74B.

*Flower size*.—Approximately 2.5 cm wide and 2 cm long.

*Reproductive organs*.—Complete pistil, anthers as cap over the pistil dropping off when flower ages. No pollen.

Disease and Insect Resistance

No known susceptibility to diseases or insects noted to date.

Comparison with the Known Cultivars

When 'Fify Violet' is compared to Impatiens 'Purple Chico' (unpatented), it is found that 'Fify Violet' exhibits a more vigorous plant habit and is also more floriferous.

When 'Fify Violet' is compared to IN-1796-3 and IN-1444-1, the parental cultivars, the flower size and plant habit are quite different. 'Fify Violet' has a smaller flower size than either parental cultivar and 'Fify Violet' also has a more compact plant habit than either of the parents.

When 'Fify Violet' is compared to 'Fify White', co-pending U.S. Plant patent application Ser. No. 09/078,641, and 'Fify Lavender', co-pending U.S. Plant patent application Ser. No. 09/078,581, the main difference is in flower color. The flower color of the instant cultivar is reddish purple while the flower color of 'Fify White' is white and the flower color of 'Fify Lavender' is much lighter purple, or lavender.

I claim:

1. A new and distinct cultivar of Impatiens plant named 'Fify Violet', substantially as described and illustrated herein, characterized particularly as to novelty by its violet flower color, small, slightly cup shaped flowers, early flowering and small-leafed basal branching growth habit.

* * * * *